United States Patent
Traboulsi et al.

(10) Patent No.: US 10,143,531 B2
(45) Date of Patent: Dec. 4, 2018

(54) SKIN MARKING POROUS GRID AND RELATED METHOD OF USE

(71) Applicant: Beekley Corporation, Bristol, CT (US)

(72) Inventors: Maeghan E. Traboulsi, Fairfax, VA (US); Thomas A. Johnson, Sandy Hook, CT (US)

(73) Assignee: BEEKLEY CORPORATION, Bristol, CT (US)

( * ) Notice: Subject to any disclaimer, the term of this patent is extended or adjusted under 35 U.S.C. 154(b) by 821 days.

(21) Appl. No.: 13/631,717

(22) Filed: Sep. 28, 2012

(65) Prior Publication Data
US 2014/0094678 A1   Apr. 3, 2014

(51) Int. Cl.
| A61B 5/05 | (2006.01) |
| A61B 90/00 | (2016.01) |
| A61B 10/02 | (2006.01) |
| A61B 6/12 | (2006.01) |

(52) U.S. Cl.
CPC .............. *A61B 90/39* (2016.02); *A61B 6/12* (2013.01); *A61B 10/0233* (2013.01); *A61B 2090/3966* (2016.02)

(58) Field of Classification Search
USPC ............ 600/425–427; 128/898; 604/19, 289, 604/290, 304–308; 378/163, 164
See application file for complete search history.

(56) References Cited

U.S. PATENT DOCUMENTS

| 3,665,918 A * | 5/1972 | Lindquist et al. .............. 602/75 |
| 4,331,727 A | 5/1982 | Maas |
| 4,918,715 A | 4/1990 | Krupnick et al. |
| 5,052,035 A | 9/1991 | Krupnick |
| 5,691,020 A | 11/1997 | Kondoh et al. |
| 5,743,899 A | 4/1998 | Zinreich |
| 5,816,269 A | 10/1998 | Mohammed |
| 6,106,852 A | 8/2000 | Vineberg |
| 6,197,420 B1 | 3/2001 | Takamizawa et al. |
| 6,198,807 B1 | 3/2001 | DeSena |
| 6,264,786 B1 | 7/2001 | Cromett |
| 6,363,940 B1 | 4/2002 | Krag |

(Continued)

OTHER PUBLICATIONS

"About Release Liners", Advanced Polymeric Coating Technologies, © 2012 Polyonics, Inc. (http://www.polyonics.com/about-liners.htm).

(Continued)

*Primary Examiner* — Amelie R Gillman
(74) *Attorney, Agent, or Firm* — McCarter & English, LLP

(57) ABSTRACT

An image guided biopsy grid markable with marking medium for marking a subject's skin underlying the grid with a marking to identify a needle entry target. The grid includes a flexible substrate and a plurality of substrate pores extending therethrough. An adhesive layer on the underside of the substrate conformingly and removably attaches the substrate to the skin substantially without gapping therebetween. The adhesive layer defines a plurality of adhesive pores and/or adhesive free spaces that allow marking medium to flow through the adhesive layer and onto the skin to mark the skin and identify the needle entry target. The biopsy grid may be marked substantially anywhere along its upper surface and marking medium will pass therethrough and mark the skin.

53 Claims, 4 Drawing Sheets

(56) References Cited

U.S. PATENT DOCUMENTS

| | | | |
|---|---|---|---|
| 6,714,628 B2* | 3/2004 | Broyles et al. | 378/164 |
| 7,232,454 B2 | 6/2007 | Rosseau | |
| 7,435,439 B2 | 10/2008 | Morgan et al. | |
| 7,435,524 B2 | 10/2008 | Anderson et al. | |
| 7,842,052 B2 | 11/2010 | Mueller et al. | |
| 8,157,807 B2 | 4/2012 | Ferren et al. | |
| 8,195,272 B2* | 6/2012 | Piferi et al. | 600/414 |
| 2003/0182815 A1 | 10/2003 | Carlson, II | |
| 2003/0187458 A1 | 10/2003 | Carlson, II | |
| 2005/0234322 A1 | 10/2005 | Lober | |
| 2006/0154031 A1 | 7/2006 | Tomlinson | |
| 2006/0169154 A1 | 8/2006 | Nelson | |
| 2007/0055290 A1 | 3/2007 | Lober | |
| 2009/0092819 A1 | 4/2009 | Malik et al. | |
| 2010/0004532 A1 | 1/2010 | Bendre et al. | |
| 2010/0313774 A1 | 12/2010 | Reiselt et al. | |
| 2011/0051892 A1 | 3/2011 | Shafer | |
| 2012/0029548 A1 | 2/2012 | Giffey | |
| 2012/0037291 A1 | 2/2012 | Goolishian | |

OTHER PUBLICATIONS

Rupp, Jürg, "Spunbond & Meltblown Nonwovens", Textile World Nonwovens/Technical Textiles, May/Jun. 2008, Billian Publishing Inc. (http://www.textileworld.com/Articles/2008/May_2008/Nonwovens/Spunbond_x_Meltblown_ Nonwovens.html).

* cited by examiner

SKIN MARKING POROUS GRID AND RELATED METHOD OF USE

FIELD OF THE INVENTION

The present invention relates to marking grids, and more particularly, to marking grids placed on a patient's skin having the capability to transmit a marking medium through the marking grid and onto the underlying skin.

BACKGROUND OF THE INVENTION

It is common in the medical field for a doctor and/or technologist to need to correlate an internal area/point of interest appearing on a radiographic image or a scan of a patient with a location on the skin surface of the patient. For example, if a doctor finds a suspicious internal mass on an image or scan, the doctor may decide to biopsy such mass, i.e., remove a portion of such mass for further testing. In order to do so, the doctor must determine where to insert a biopsy needle at the skin surface in order to contact the mass below. Once that determination is made, the insertion point is marked on the skin. Typically, this is done with a type of marking medium, e.g., a permanent or semi-permanent ink, or a small adhesive marker is attached to the skin.

One approach to identifying the area/point of entry at the skin surface of the patient is to place a radiopaque grid on the skin surface of a patient and radiographically image or scan, cross-sectionally, i.e., in a plane normal to the skin surface of the patient, through the grid and the patient's body underneath the grid. Resultant cross-sectional images or scans provide sequential cross-sectional slices of the imaged area, with the series of radiopaque grid lines appearing in the cross-sectional slices as a series of dots atop the skin surface. Each dot corresponds to a "y" coordinate point (see, for example, the reference coordinate system in FIG. 2). A doctor or technologist may then view the resultant imaging slices and determine the most appropriate slice(s) from which to identify the area/point of interest relative to the grid lines. A doctor or technologist may view the sequential cross-sectional imaging slices electronically, such as via a computer. Each subsequent cross-sectional imaging slice corresponds to a subsequent axial position or "x" coordinate point (see, for example, the reference coordinate system in FIG. 2) along the grid, i.e., the distance along the grid lines to which the respective slice corresponds. Accordingly, when the most appropriate slice(s) are determined by the doctor or technologist, the axial position of the slice(s) is identified on the grid. For example, the computer may shine a laser along the grid, such as, for purposes of example only, line A-A of FIG. 2, showing the axial position of the slice(s). Having determined the "x" coordinate point of the desired entry point on the skin, the "y" coordinate point for the desired entry point on the skin can be identified relative to the grid line dots using the selected imaging slice(s). However, in order to mark the skin, the grid must be removed. This can impede the accuracy of the placement of the mark, because once the grid is removed, the doctor or technologist no longer has the visible grid lines to use as a reference point.

Prior art attempts to solve the problem include grids that include plural openings, e.g., holes or slits in the grid at intersections of various grid lines so that a marking instrument, e.g., a marking pen, can be applied therethrough to mark the skin surface. One problem the inventors recognized with such a grid is that the underlying surface cannot be marked at substantially any point. Rather, the skin surface can only be marked at locations where one of the openings or slits in the grid is located. Thus, unless the desired marking point coincidentally coincides with one of the slits, the exact desired marking point cannot be marked. A doctor and/or technologist can only mark the skin surface at the closest slit to the identified area/point of interest. Such marking may be detrimentally inaccurate, depending on the size of the internal point of interest, making the biopsy more difficult.

Another prior art attempt to solve the problem is to use a porous grid material so that marking medium can be applied to the grid and pass through the grid to mark the skin. This permits a mark to be placed anywhere on the grid, and thus the skin. However, the inventors recognized that these grids still have several problems. Typically, grids are attached to the skin surface "SS" with an adhesive, such as a medical adhesive. These prior art devices utilize thin adhesive strips at opposing ends of the device to attach the device to an underlying surface. The device thus attaches to the underlying skin surface SS only at those opposing ends. Between the ends, however, the device may not conform to the contours of the skin but rather leave gaps between the device and skin and/or cause wrinkling of the device. Wrinkling and/or gapping of the device result in radiographic images or scans having grid lines or markings that are spaced away from the skin surface SS (as shown by some of the dots GL in FIG. 1). This gapping makes it more difficult for the technologist to correctly correlate the area of interest with the patient's skin surface SS because the references in the image, i.e., the dots GL, are not at the skin surface. In effect, the technologist must guess how to compensate for the gap between the gridlines and the skin when marking the skin. Gapping also increases the risk of inaccurate or incomplete marking. A gap or wrinkle can prevent marking medium placed on the grid from reaching the skin surface. Another problem the inventors recognized with the thin adhesive strips is that the adhesive bond between the grid and the underlying surface is not very strong. As the grid is intended to remain on the skin temporarily, perhaps a few hours at most, the adhesive is of a type that allows the grid to be removed fairly easily. Accordingly, the grid is susceptible to inadvertent movement such as sliding on the skin or detaching from the skin, thereby causing inaccuracies in the marked locations. Such inaccuracies increase the likelihood of having to repeat at least part of a procedure, such as, for example, a CT-guided biopsy, resulting in wasted time and materials, and more importantly, undue pain and discomfort for a patient.

It is an object of the present invention to overcome one or more of the above-described drawbacks and/or disadvantages of the prior art marking grids.

SUMMARY OF THE INVENTION

In one aspect, an image-guided biopsy grid comprises a flexible substrate defining a first side, a second side opposite the first side, and a plurality of substrate pores extending between the first and second sides that allow marking medium applied to the first side of the substrate to flow through to the second side of the substrate. The grid further comprises a plurality of at least partially radiopaque grid lines spaced relative to each other on the first side of the flexible substrate, wherein the flexible substrate extends substantially throughout the spaces between a plurality of adjacent grid lines. The grid lines allow marking medium applied to a grid line to flow at least one of (i) through or (ii) around the grid line and to the substrate or skin. The grid further comprises an adhesive-containing adhesive layer on the second side of the substrate, wherein the adhesive layer is configured and adapted to enable the substrate to be conformingly and removably attached to the skin substantially without gapping therebetween, and to allow marking medium flowing through the substrate to flow through the adhesive layer and onto the skin to mark the skin and identify the needle entry target. The grid is thus markable with a marking medium for marking the grid and the subject's skin underlying the grid with the marking medium to identify a needle entry target.

In some embodiments, the plurality of grid lines define a plurality of grid line pores extending through respective grid lines that allow marking medium applied to a grid line to flow through said grid line.

In some embodiments, the marking on the skin is substantially the same size and shape as a corresponding marking applied to the first side of the substrate.

In some embodiments, the flexible substrate extends substantially throughout the spaces between adjacent grid lines.

In some embodiments, the flexible substrate is rectangular, and the grid lines are spaced relative to each other and extend approximately from one side of the substrate to the other.

In some embodiments, the grid is configured to allow a marking applied to the first side of the substrate or a grid line to pass substantially directly through the substrate and adhesive layer of the grid and mark the skin. In some embodiments, the grid is configured to allow a marking applied to the first side of the substrate or a grid line to pass substantially simultaneously through the substrate and adhesive layer of the grid and mark the skin.

In some embodiments, the adhesive covers at least about 30% of the surface area of the second side of the substrate. In some such embodiments, the adhesive covers substantially the entire second side of the substrate.

In some embodiments, the substrate is a non-woven layer. In some embodiments, the non-woven substrate layer defines a basis weight within the range of about ⅖ oz/yd$^2$ to about 1 oz/yd$^2$. In some such embodiments, the non-woven substrate layer defines a basis weight within the range of about ½ oz/yd$^2$ to about ⅘ oz/yd$^2$. In some embodiments, the non-woven substrate layer defines a thickness of less than about 25 mils.

In some embodiments, the plurality of grid lines define a line width along a substantial portion of each line of less than about ⅛ inch. In some embodiments, the plurality of grid lines define a line thickness along a substantial portion of each line within the range of about ½ mil to about 2 mils. In some embodiments, the plurality of grid lines define a radiopaque material density along a substantial portion of each line of at least about 3 grams/cm$^3$.

In some embodiments, the adhesive layer requires a maximum force of about 50 oz/in to peel from the skin. In some embodiments, the adhesive layer defines a bond strength between the adhesive layer and the substrate that is at least about 5% greater than a bond strength between the adhesive layer and the skin. In some such embodiments, the bond strength between the adhesive layer and the substrate is at least about 15% greater than the bond strength between the adhesive layer and the skin.

In some embodiments, the adhesive defines a plurality of adhesive pores configured to allow marking medium flowing through the substrate to flow through the adhesive pores and onto the skin to mark the skin and identify the needle entry target. In some such embodiments, the adhesive pores define at least one of (i) substantially isolated channels and (ii) interconnected channels, configured so that the mark on the skin at least substantially corresponds in location, shape, and size to a corresponding marking applied to the first side of the substrate or a grid line.

In some embodiments, the adhesive layer defines a plurality of spaces between adhesive, configured to allow marking medium flowing through the substrate to flow around the adhesive and through the spaces therebetween and onto the skin to mark the skin and identify the needle entry target.

In some embodiments, the grid further comprises a release liner that is releasably attachable to an underside of the adhesive layer. In some such embodiments, the release liner defines a thickness within the range of about 1 mil to about 10 mils. In some embodiments, the release liner includes a friction modifier on an upper side and/or an opposing underside thereof.

In accordance with another aspect, an image-guided biopsy grid comprises a flexible substrate defining a first side and a second side opposite the first side and first means for allowing marking medium applied to the first side of the substrate to flow through to the second side of the substrate. The grid further comprises a plurality of at least partially radiopaque grid lines located on the first side of the flexible substrate and defining spaces therebetween, wherein the flexible substrate extends substantially throughout a plurality of spaces between adjacent grid lines and wherein the grid lines allow marking medium applied to a grid line to flow at least one of (i) through or (ii) around the grid line and to the substrate or skin. The grid further comprises an adhesive-containing adhesive layer on the second side of the substrate configured and adapted to enable the substrate to be conformingly and removably attached to the skin substantially without gapping therebetween, and second means for allowing marking medium flowing through the substrate to flow through the adhesive layer and onto the skin for marking the skin and identifying the needle entry target. The grid is thus markable with a marking medium for marking the grid and the subject's skin underlying the grid with the marking medium to identify a needle entry target.

In some embodiments, the flexible substrate extends substantially throughout the spaces between adjacent grid lines.

In some embodiments, the adhesive layer covers at least the portions of the second side of the substrate underlying the grid lines and spaces between adjacent grid lines.

In some embodiments, the second means is for marking the skin with a mark that is substantially the same size and shape as a corresponding marking applied to the first side of the substrate.

In some embodiments, the first means is a plurality of substrate pores extending between the first and second sides of the substrate, and the second means is a plurality of spaces extending through the adhesive layer between adhesive; and the grid lines are non-lead.

In some embodiments, the first means is a plurality of substrate pores extending between the first and second sides of the substrate, and the second means is a plurality of adhesive pores extending through the adhesive of the adhesive layer; and the grid lines are non-lead.

In some embodiments, the adhesive covers at least about 30% of the surface area of the second side of the substrate.

In some embodiments, the grid lines define third means for allowing marking medium applied to a grid line to flow through said grid line. In some such embodiments, the third means is a plurality of grid line pores extending through the grid lines.

In some embodiments, the multilayer device is configured to allow a marking applied to the first side of the substrate or a grid line to pass substantially directly through the substrate and adhesive layer of the grid and mark the skin.

In some embodiments, the multilayer device is configured to allow a marking applied to the first side of the substrate or a grid line to pass substantially simultaneously through the substrate and adhesive layers and mark the skin.

In some embodiments, the grid further comprises fourth means for protecting said second means. In some such embodiments, the fourth means is a release liner releasably attached to the second means.

In accordance with another aspect, a method comprises the following steps:

(i) adhesively and conformably attaching a second side of a flexible substrate to a person's skin, wherein the substrate includes a plurality of at least partially radiopaque grid lines spaced relative to each other on a first side of the substrate opposite the second side; and (ii) marking the first side of the substrate with reference to one or more of the grid lines with a marking medium that passes through both the substrate and an adhesive-containing adhesive layer underlying the substrate and marks the skin.

In some embodiments, the method further comprises the step of imaging a portion of the person's body and substrate attached to the body, and identifying a needle entry target with reference to one or more of the grid lines. Further, step (ii) includes marking the first side of the substrate with the marking medium at the needle entry target so that the marking medium passes through both the substrate and an adhesive layer underlying the substrate and marks the needle entry target on the skin. In some embodiments, the method further comprises the steps of removing the substrate from the skin and inserting a biopsy needle substantially at the marked needle entry target on the skin.

In some embodiments, the marking on the skin is substantially the same size and shape as the corresponding marking applied to the first side of the substrate.

In some embodiments, step (ii) includes the marking medium passing through a plurality of pores extending through the substrate, and a plurality of pores or spaces between adhesive extending through the adhesive layer underlying the substrate. In some such embodiments, step (ii) also includes the marking medium passing through a plurality of pores extending through at least one grid line and/or around said at least one grid line. In some such embodiments, step (ii) includes the marking medium passing substantially directly through the substrate and an adhesive layer to mark the skin. In other such embodiments, step (ii) includes the marking medium passing substantially simultaneously through the substrate and an adhesive layer to mark the skin.

In some embodiments, step (i) includes adhesively attaching the second side of the substrate to the skin with an adhesive covering substantially the entire second side of the substrate underlying the grid lines and spaces between adjacent grid lines.

In some embodiments, a release liner is attached to the substrate prior to use, and the method further comprises the step of removing the release liner from the substrate prior to step (i).

In some embodiments, the marking step includes applying an ink pen to the first side of the substrate.

One advantage of the current inventive marking grid is that it allows a marking made substantially anywhere along the grid to transmit accurately, and at least in some embodiments, substantially simultaneously, to the underlying surface, such as, for example, a skin surface. Another advantage of the marking grid is that it is sufficiently flexible to conform to the contours of the skin surface when placed thereon, substantially without wrinkling, folding, buckling or distorting. Yet another advantage of the marking grid is that it remains attached and stays in place on the underlying surface until manually peeled away. These features allow for an accurate and efficient manner to register, i.e., localize, a needle entry site when performing a medical procedure, such as, for example, a CT-guided biopsy, with minimal inconvenience to the patient.

Other objects and advantages of the present invention, and/or of the currently preferred embodiments thereof, will become more readily apparent in view of the following detailed description of the currently preferred embodiments and accompanying drawings.

DETAILED DESCRIPTION OF EMBODIMENTS OF THE INVENTION

Embodiments of the invention are described herein in conjunction with the drawings provided herein. The embodiments disclosed herein are to be considered exemplary of the principles of the present invention described herein. Various modifications will be apparent to those skilled in the art based on the teachings herein without departing from the scope or spirit of the invention disclosed herein.

The term "pen" is used herein to mean without limitation any of various instruments for marking, writing or drawing with ink or a similar substance. In one embodiment, the pen has its own ink-source, and a tip made of porous, pressed fibers, such as felt. The term "marking medium" is used herein to mean any substance capable of marking, such as, for example, without limitation, ink or dye. The term "ink" is used herein to mean without limitation a fluid or viscous or other substance used for marking, writing or printing. One pen that can be used in connection with the present invention is the marker sold under the trademark SHARPIE® by Newell Rubbermaid Office Products of Oak Brook, Ill. The term "grid lines" is used herein to mean without limitation a plurality of spaced lines or other markings, which may be used, for example, to localize a needle entry site for any of numerous different types of procedures, including without limitation any of numerous different types of image-guided procedures, such as computed tomography ("CT"), magnetic resonance imaging ("MRI") and x-ray procedures, including without limitation image-guided biopsy procedures, and drainage procedures, on any of numerous different body parts, including without limitation thyroid, lung, liver, abdominal, pelvic and extremity biopsies and drainages. The term "needle" is used herein to mean without limitation any of numerous different slender, pointed, instruments made of any of numerous different materials, such as steel or plastic, that are used to pierce tissues, which may be used for any of numerous different procedures when piercing tissues, including without limitation injecting a substance into tissue, withdrawing a substance from tissue, suturing and/or otherwise operating on tissue.

Figure 2:
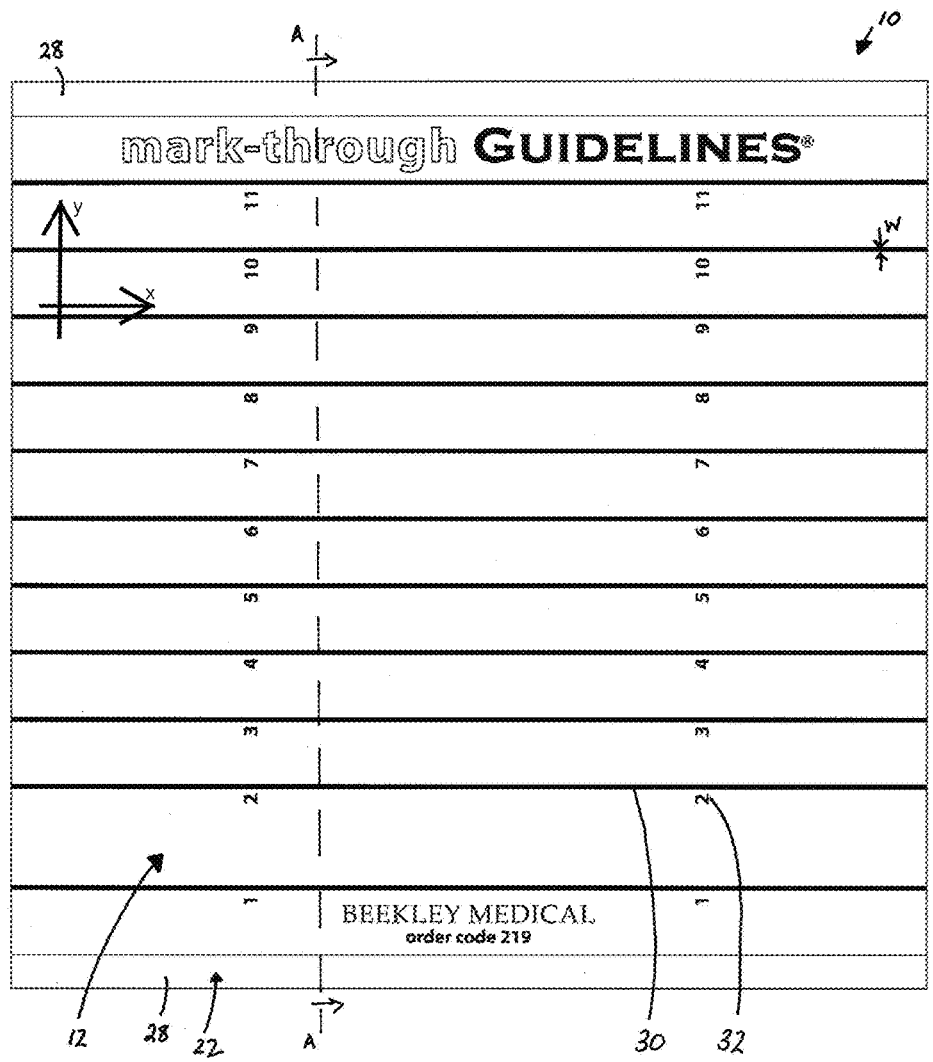
FIG. 2 is a top view of a substantially flexible and porous marking grid.
Figure 3:
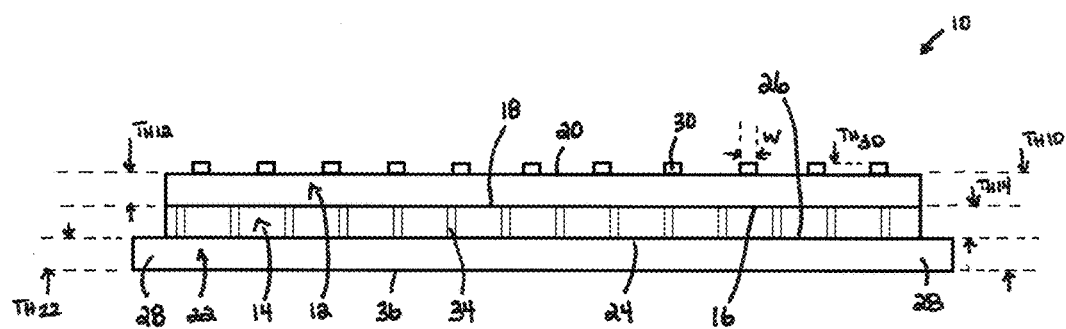
FIG. 3 is a schematic cross-sectional view of the marking grid of FIG. 1 along the line A-A.

In FIGS. 2 and 3, a porous skin marking grid is indicated generally by the reference numeral 10. The skin marking grid 10 defines a patch or sheet that includes a substrate or label layer 12 and an adhesive layer 14 attached at a first or upper side 16 thereof to a second side or underside 18 of the substrate layer 12. In the illustrated embodiment, the marking grid 10 is substantially rectangular. The marking grid 10 generally defines a surface area within the range of about 4 square inches and about 144 square inches. The grid 10 also defines a thickness $TH_{10}$ within the range of about 5 mils to about 40 mils. However, as will be appreciated by those of ordinary skill in the art, other marking grid size and thickness may also be utilized according to the desired application, such as, for example, the part of the body to which the grid is to be applied and the size of the field for the radiographic image or scan.

Both the substrate layer 12 and the adhesive layer 14 are sufficiently flexible to conformably place the grid 10 atop an underlying curvilinear surface, e.g., the skin surface of a patient, substantially without wrinkling, folding, buckling, distorting or gapping between the grid 10 and the skin surface. The adhesive is sufficiently distributed over the underside 18 of the substrate layer 12 in a sufficient amount to sufficiently hold the grid 10 to the contours of the skin surface, e.g., substantially without wrinkling or leaving gaps therebetween.

As is described further below, both the substrate layer 12 and the adhesive layer 14 are sufficiently porous, i.e., define sufficient apertures, pores, spaces or channels therethrough, to allow a marking or writing made on the substrate layer 12 with a marking instrument, such as, for example, a felt tip pen, to pass through both layers 12, 14, and substantially accurately mark the underlying skin surface at approximately the same location and with approximately the same dimensions, i.e., approximately the same size and shape, as the mark made on the first or upper side 20 of the substrate layer 12.

The skin marking grid 10 also includes a release liner 22, releasably attached at an upper side 24 thereof to an underside 26 of the adhesive layer 14. The release liner 22 extends over the entire underside of the marking grid 10 and includes portions extending beyond opposing ends of the grid 10, providing opposing exposed areas 28 as shown in FIGS. 2 and 3. The exposed areas can be grasped, e.g., manually by a user, to peel the liner 22 away from the marking grid 10, exposing the underside 26 of the adhesive layer 14 for attachment of the grid 10 to the skin surface.

In the illustrated embodiment, the substrate layer 12 is a non-woven material, and is formed of a non-woven polymeric material such as, for example, a porous non-woven PET (polyethylene) material. However, as should be recognized by those of ordinary skill in the pertinent art based on the teachings herein, the substrate layer 12 may be formed of any porous material, currently known or that later becomes known, capable of performing the functions of the substrate layer. That is, and as described further herein, the substrate layer allows a marking medium, e.g., ink, to pass substantially directly therethrough without bleeding or laterally spreading out, which would otherwise decrease the amount of ink which ultimately reaches the skin and decrease the accuracy of the mark on the skin surface. It will also be appreciated by those of ordinary skill in the pertinent art that the non-woven layer may be made via any of numerous different suitable processes, such as, for example, but not limited to, the spunbonding, flashspinning, and meltblown processes.

In some exemplary embodiments, the basis weight of the non-woven substrate layer 12 is within the range of about ⅖ oz/yd$^2$ to about 1 oz/yd$^2$. In some such embodiments, the basis weight of the substrate layer 12 is within the range of about ½ oz/yd$^2$ to about ⅘ oz/yd$^2$. In yet some such embodiments, the basis weight of the substrate layer 12 is about ⅗ oz/yd$^2$. The thickness $TH_{12}$ of the substrate layer 12 is less than about 25 mils. In some exemplary embodiments, the thickness of the substrate layer 12 is less than about 15 mils. In some such embodiments, the thickness of the substrate layer 12 is less than about 10 mils. In yet some such embodiments, the thickness of the substrate layer is less than about 7½ mils. It should be appreciated by those of ordinary skill in the pertinent art that the overall porosity or capacity of a non-woven material to permit the marking medium to pass through is more dependent upon the basis weight of the material, rather than thread count or pore size due to the non-uniform pore structure. That being said, the thickness, basis weight, thread count, pore size and/or pore configuration of the material can be selected to achieve a desired porosity.

Testing performed by the current inventors has shown that the combination of the above-described basis weight and thickness of the non-woven layer 12 achieved unexpected results, allowing a marking with a marking medium, e.g., ink marking, made thereon, such as, for example, a dot, an "X", a shape, a pattern, or substantially continuous writing, to pass through the layer 12 substantially simultaneously upon marking the non-woven layer 12. This allows a user to make the necessary marking onto the non-woven layer 12 at a substantially normal speed, and the necessary amount of ink will pass therethrough to mark the underlying surface. The current inventors have also found that the combination of the above-described features of the non-woven layer 12 achieve unexpected results, allowing such an ink marking to flow substantially directly, i.e., without bleeding or laterally spreading out, through the non-woven layer 12 from an upper surface thereof to the lower surface thereof, rather than flowing tortuously or laterally within the layer. This allows the marking to substantially maintain its original dimensions and location upon passage through the layer.

In some embodiments, the substrate layer 12 further includes grid lines 30 and grid line numerals 32 located on an opposite, upper, or first, side 20 of the substrate layer 12 relative to the adhesive layer 14, as shown in FIGS. 2 and 3. As seen FIG. 2, the grid lines 30 and the numerals visually contrast with the substrate 12 and/or the patient's skin for viewing and reading by the user. The substrate layer 12 extends substantially throughout the spaces between the grid lines 30. In the illustrated embodiment, the grid lines 30 extend approximately from one side of the substrate layer 12 to the other. Alternatively, some or all of the grid lines 30 may extend only along a portion of the substrate layer 12, and not from one side of the substrate layer to the other.

The grid lines 30 include an at least partially radiopaque material, in order to be visible in a radiographic image or scan. In one such exemplary embodiment, the grid lines 30 may be formed of respective lengths of a tape, as a backing for the grid lines, having particles of radiopaque powder applied to or embedded in a top surface thereof. One example of a suitable tape backing is, without limitation, a cellophane based tape. The tape is applied, via its opposing bottom surface, to the upper surface 20 of the substrate layer 12. As another example, the grid lines 30 may be formed of a radiopaque ink, such as, for example, but not limited to, tungsten non-lead radiopaque ink. One example of a suitable radiopaque ink used for the grid lines 30 is tungsten non-lead radiopaque ink sold by Creative Materials, Inc. of Ayer, Mass. In some such embodiments, the ink is printed onto the substrate layer 12. The inventors have found that use of such ink results in porous grid lines 30.

Figure 1:
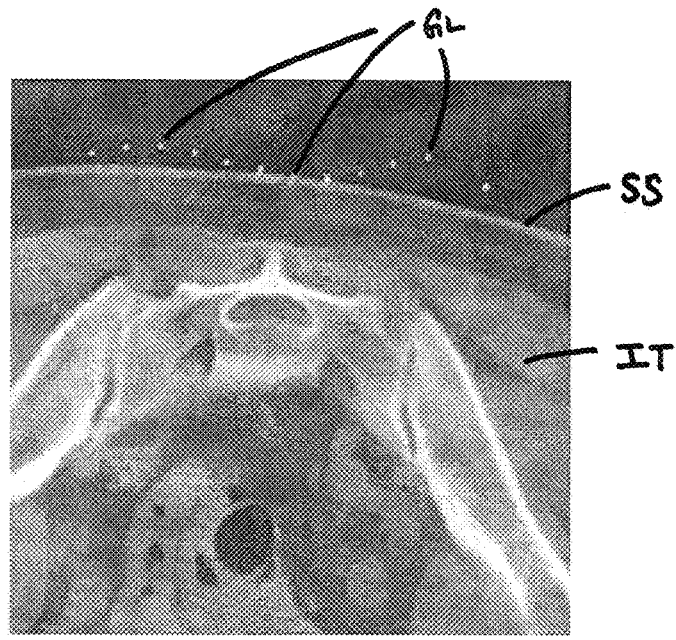
FIG. 1 is a radiographic image slice, showing a cross-section of a prior art marking grid attached to the skin surface of a patient and the gapping present therebetween.
Figure 4:
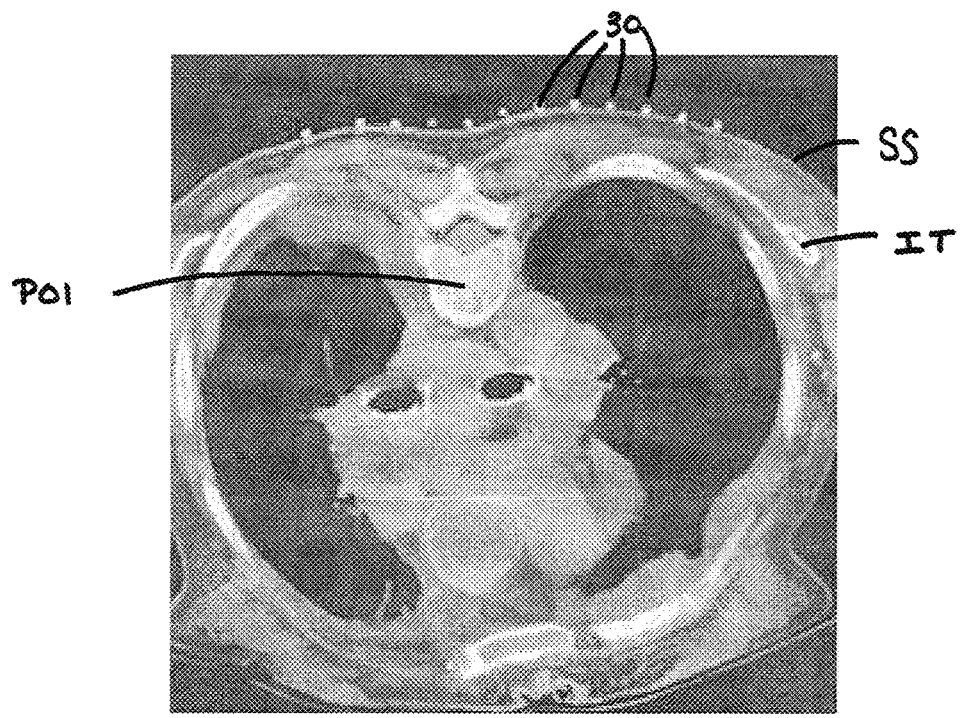
FIG. 4 is a radiographic image slice, showing a cross-section of the marking grid of FIG. 2 attached to the skin surface of a patient.

In the embodiment of FIG. 2, the grid lines 30 are substantially parallel. The direction in which the grid lines 30 run is referred to herein as the "x" direction. The direction that is perpendicular to the direction of the grid lines 30 is referred to herein as the "y" direction. The "x" and "y" directions shown in FIG. 2 are for reference only. They do not appear on the grid itself. In the embodiment of FIG. 2, the grid line labeled number 1 and the grid line labeled number 2 are spaced differently than the spacing between any other two adjacent grid lines 30. As shown in FIG. 2, the grid line numbered 1 and the grid line numbered 2 are spaced farther apart than the remaining adjacent grid lines. Accordingly, as seen in FIG. 4, the differently spaced grid lines appear differently spaced in the image or scan. This provides an indicator of grid orientation in a cross-sectional radiographic image or scan, i.e., to indicate which of the two outermost dots correspond to grid line numbered 1 and to the last numbered grid line at the opposing side of the grid, respectively. As should be recognized by those of ordinary skill in the art, the grid lines numbered 1 and 2 may also be spaced nearer to one another than the remaining adjacent grid lines to indicate orientation. Alternatively, the grid lines at the opposing end of the grid, such as, for example, gridlines numbered 10 and 11 in FIG. 4, may be spaced differently than the spacing between any other two adjacent grid lines 30. In yet other embodiments, all the grid lines are substantially equally spaced from each other.

In some embodiments, the numerals 32 also include an at least partially radiopaque material. Alternatively, the numerals 32 may include a non-radiopaque material, partially radiopaque material, or partially radiolucent material. As should be recognized by those of ordinary skill in the pertinent art based on the teachings herein, any radiopaque material, currently known or that later becomes known, including any lead based radiopaque material capable of performing the function of the radiopaque material described herein, may be utilized. In some embodiments, the numerals 32 are printed onto the substrate layer 12.

Generally, the grid lines 30 define a line width W along a substantial portion of each line of less than about 125 mils. In some embodiments, the grid lines 30 define a line width along a substantial portion of each line of less than about 80 mils. In some such embodiments, the grid lines 30 define a line width along a substantial portion of each line of less than about 50 mils. In yet some such embodiments, the grid lines 30 define a line width along a substantial portion of each line within the range of about 20 mils to about 40 mils. In yet some such embodiments, the grid lines 30 define a line width along a substantial portion of each line of about 30 mils. The width W of the grid lines is selected so as to be visible to the user and also on the radiographic image or scan, yet reduce blocking or obscuring the visible surface of the skin or underlying tissue in the image or scan. Those of ordinary skill in the art should understand that the width of the lines can be selected as appropriate for the intended application.

In some of the above-described exemplary embodiments, the grid lines 30 also define a thickness $TH_{30}$, along a substantial portion of each line within the range of about ½ mil to about 2 mil. In some such embodiments, the grid lines 30 define a thickness within the range of about ⅘ mil to about 1½ mil. In yet some such embodiments, the grid lines 30 define a thickness within the range of about 9/10 mil to about 1⅕ mil. In some such embodiments, the grid lines 30 define a thickness of about 1 mil.

In yet some of the exemplary embodiments described above, the grid lines 30 define a radiopaque material density along a substantial portion of each line of at least about 3 grams/cm³. In some such embodiments, the grid lines 30 define a radiopaque material density of at least about 4 grams/cm³. In yet some such embodiments, the grid lines 30 define a radiopaque material density of at least about 5 grams/cm³.

Those of ordinary skill should understand that the grid line width and thickness, in combination with the radiopaque material density, contribute to the radiopacity of the grid lines, and thus the degree to which the lines and/or numerals are visible on a radiographic image or scan. That is, as thickness and/or density increases, the radiopacity increases. The thickness and density can thus be selected to provide a desired radiopacity for the application, e.g., the radiation power and exposure time used for the type, location and depth of tissue being imaged.

Testing performed by the current inventors has shown that the combination of the above-described features of the grid lines 30 results in substantially the least amount of radiopaque material that may be used, per line, while also appearing substantially visible in a radiographic image or scan. That is, the grid lines 30 appear as a substantially solid or continuous line in an image or scan, such as, for example, in an X-ray image, and also appear in substantially all consecutive cross-sectional image slices of interest in, for example, a CT scan. One advantage of utilizing substantially the least amount of radiopaque material for the grid lines 30 is to minimize the portions of the image or scan covered by the lines. Additionally, due to the expense of the radiopaque material used, such as, for example, non-lead tungsten radiopaque ink, another advantage of using substantially the least amount of radiopaque material for the grid lines 30 is to reduce manufacturing costs of the marking grid 10. As mentioned above, though, less or more radiopaque material can be used as suitable for a particular application.

The current inventors have also found that the combination of the above-described width, thickness, composition and density of the grid lines 30 achieved unexpected results. In some embodiments, the grid lines 30 are substantially porous, i.e., define pores extending therethrough. The combination of the above-described width, thickness, composition and density of the grid lines 30 substantially allows marking medium placed on the grid lines 30 to pass through pores of grid lines 30 and through the underlying substrate layer 12. Due to the porosity of the substrate layer 12, marking medium can also flow substantially directly around the grid lines 30 to and through the substrate layer. That is, the marking medium can flow to and/or along the edges of the grid lines 30 to the underlying substrate layer 12.

In other embodiments, the grid lines 30 are substantially not porous. Nonetheless, the above-described combination of width, thickness and composition of the grid lines 30 allows marking medium placed on the grid lines 30 to flow substantially directly around the grid lines 30 to the underlying substrate layer 12 as discussed above. Accordingly, substantially any point on the upper surface 20 of the substrate layer 12, including any point directly atop a grid line 30, may be marked and marking medium will pass through the layer.

The current inventors have also found that the combination of the above-described width, thickness, composition and density of the grid lines allows the marking grid 10 to remain flexible enough to conform to an underlying curvilinear surface contour substantially without wrinkling, folding, buckling, distorting or gapping between the grid 10 and the underlying surface. The thickness of the grid lines 30 does not overly stiffen the grid 10. As should be recognized by those of ordinary skill in the pertinent art based on the teachings herein, different combinations of line width, thickness and radiopaque material density, capable of performing the functions of the grid lines as described herein, may also be utilized, as appropriate for the particular application.

The adhesive layer 14, defining a thickness $TH_{14}$, is attached to the underside 18 of the substrate layer 12 and cooperates with the substrate layer 12, and the grid lines 30, to allow a marking medium passed substantially directly and, at least in some embodiments, substantially simultaneously through the substrate layer 12 to continue substantially directly and, at least in some embodiments, substantially simultaneously through the adhesive layer 14 and accurately mark the underlying surface at approximately the same location and with approximately the same dimensions as the mark on the substrate 12. The adhesive layer 14 also cooperates with the substrate layer 12 to allow the marking grid 10 to conform to an underlying curvilinear surface contour substantially without wrinkling, folding, buckling, distorting or gapping between the grid 10 and the surface, as shown in FIG. 4.

In some exemplary embodiments, the adhesive may, without limitation, be applied to the underside 18 of the substrate layer 12 in the form of a pattern and/or a matrix. The adhesive layer 14 may, for example, be distributed along the underside 18 of the substrate layer 12 in a series of rows and/or columns, of adhesive dots and/or lines, defining adhesive-free spaces therebetween. Such adhesive-free spaces extend substantially from the upper side 16 of the adhesive layer 14, i.e., the side adjacent the substrate layer 12, to the opposing underside 26 of the adhesive layer 14. Generally, adhesive lines define a width along a substantial portion of each line within the range of about 10 mils to about 50 mils. In some embodiments, the adhesive lines define a line width along a substantial portion of each line within the range of about 20 mils to about 40 mils. In some such embodiments, the adhesive lines define a line width along a substantial portion of each line of about 30 mils. Similarly, adhesive dots generally define a diameter within the range of about 10 mils to about 50 mils. In some embodiments, the adhesive dots define a diameter within the range of about 20 mils to about 40 mils. In some such embodiments, the adhesive dots define a diameter of about 30 mils. As should be appreciated by those of ordinary skill in the pertinent art, the dots and/or lines of adhesive are spaced as necessary with respect to one another to substantially prevent lifting, gapping or wrinkling between the grid 10 and the skin surface.

In some such exemplary embodiments, the adhesive layer 14 covers at least about 30% of the surface area of the underside 18 of the substrate layer 12. In some such embodiments, the adhesive layer 14 covers at least about 50% of the surface area of the underside 18 of the substrate layer 12. In some other such embodiments, the adhesive layer 14 covers at least about 75% of the surface area of the underside 18 of the substrate layer 12. In yet some other embodiments, the adhesive layer 14 covers at least about 90% of the surface area of the underside 18 of the substrate layer 12. In yet further embodiments, the adhesive layer 14 covers substantially the entire surface area of the underside 18 of the substrate layer 12. As shown in FIG. 3, the adhesive is not just located along the edges of the substrate layer 12, but distributed substantially over the underside 18 of the substrate layer 12. As may be recognized by those of ordinary skill in the pertinent art based on the teachings herein, the adhesive may be applied to the underside of the substrate layer 12 in any of numerous patterns or arrangements, and amounts, currently known or that later become known, enabling the adhesive layer 14 to perform the function(s) as described herein, namely, sufficiently attaching the grid 10 to the skin surface, e.g., substantially without lifting, gapping or wrinkling therebetween.

In yet some such exemplary embodiments, the adhesive utilized in the adhesive layer 14, such as, by way of example only, that disclosed in U.S. patent application Ser. No. 12/247,621, filed Oct. 8, 2008, entitled "Porous Pressure Sensitive Adhesive and Tapes," which is hereby expressly incorporated by reference in its entirety as part of the present disclosure, includes a plurality of pores 34 therethrough. Pores 34 are schematically shown, in an enlarged view for clarity, which is not drawn to scale, in FIG. 3. The pores 34 extend substantially from the upper side 16 of the adhesive layer 14 to the opposing underside 26 of the adhesive layer 14, as shown in FIG. 3. In the schematic illustration in FIG. 3, the pores 34 form isolated channels extending substantially directly through the adhesive layer 14. Such pores 34 are substantially surrounded by adhesive and substantially do not interconnect. That is, the pores 34 do not communicate with one another. The marking medium substantially does not move laterally from one pore 34 to another. Other embodiments contain pores that are interconnected, or even form an interconnected network of channels. Certain embodiments contain both pores that are isolated and pores that are interconnected. Regardless, the pores are configured to permit fluid, such as the marking medium, after passing through the substrate layer 12, to continue through the pores 34 of the adhesive layer 14 and mark the underlying surface at substantially the same location with substantially the same shape and dimensions. That is, the marking medium does not move laterally to a degree sufficient to substantially affect the location, size and dimensions of the mark on the skin, and a sufficient amount of medium to form the marking on the skin passes through the grid 10. In some embodiments, the location and volume of the pores 34 are substantially uniformly distributed through the adhesive layer 14, allowing substantially consistent marking to be made anywhere on the grid 10. One example of a suitable adhesive used for the adhesive layer 14 is the porous adhesive sold under the trademark ARCARE® by Adhesive Research, Inc. of Glen Rock, Pa.

In embodiments where the adhesive utilized in the adhesive layer 14 is porous, i.e., includes pores 34 extending therethrough, the pores 34 allow a marking medium flowing through the substrate layer 12 to flow through the adhesive layer 14, via the pores 34, and onto the skin. The inventors have found that the above-described width and diameter of the adhesives lines and/or dots also allows marking medium to flow substantially directly around the rows and/or columns of adhesive dots and/or lines to the underlying skin surface, via the adhesive-free spaces therebetween. That is, the marking medium can flow through and/or along the edges of the adhesive dots and/or lines to the underlying skin surface.

In other embodiments, the adhesive utilized in the adhesive layer 14 is substantially not porous. Nonetheless, and as previously described, the width and diameter of the adhesive lines and/or dots allows the marking medium flowing through the substrate layer 12 to flow substantially directly around the rows and/or columns of adhesive dots and/or lines to the underlying skin surface, via the adhesive-free spaces therebetween. Accordingly, marking medium flowing substantially anywhere through the substrate layer 12 will not be impeded by the underlying adhesive layer 14, and will continue through the layer 14 to the underlying skin at substantially the same location and with approximately the same dimensions.

As mentioned above, because the adhesive layer 14 underlies the substrate layer 12, as opposed to the prior art, it substantially attaches and conforms the substrate layer to the contours of the underlying surface.

In some exemplary embodiments, the adhesive bond between the adhesive layer 14 and the underlying surface, i.e., the surface that the marking grid 10 is placed on such as skin, requires a maximum force of about 50 ounces per 1 inch of adhesive width (oz/in) to peel the adhesive layer 14 from the surface. In some such embodiments, the adhesive bond between the adhesive layer 14 and the underlying surface requires a maximum force of about 25 oz/in to peel the adhesive layer 14 from the surface. In yet some such embodiments, the adhesive bond between the adhesive layer 14 and the underlying surface requires a maximum force of about 10 oz/in to peel the adhesive layer 14 from the surface. In yet some such embodiments, the adhesive bond between the adhesive layer 14 and the underlying surface requires a force within the range of about 4 oz/in and about 6 oz/in to peel the adhesive layer 14 from the surface.

Testing performed by the current inventors has shown that bond strength within the above-described range to peel the marking grid 10 away from an underlying surface, such as, for example, the skin surface of a subject, is strong enough to remain securely attached to the underlying surface during usage of the marking grid 10 without inadvertently moving, sliding, or detaching from the skin surface, which can cause undesirable wrinkling, folding or gapping. The current inventors have also found that the above-described range of bond strength will not cause undue pain or injury to the subject or patient when removing the marking grid 10.

It should be appreciated by those of ordinary skill in the pertinent art that adhesive peel strength tests, according to the American Society for Testing and Materials standards, are typically conducted on test strips that are 1 inch wide. The force required to peel the adhesive off of/away from another surface, such as, for example, another layer of the device or an underlying surface, is measured after the adhesive has been attached to the surface for five minutes. The total removal force thus depends on the total adhesive area in contact with the underlying surface, and, to some degree, the characteristics of that surface. A desired removal force can be achieved by the selection of the peel strength of the adhesive to suit the particular application, e.g., the size of substrate 12 and adhesive area.

In the illustrated embodiment, the bond force of the adhesive layer 14 to the substrate 12 is greater than the bond force to an underlying surface upon which the adhesive layer 14 is placed. Accordingly, the adhesive layer 14 substantially does not separate from the substrate 12 when the liner 22 is removed from the grid 10 or when the grid 10 is removed from the patient's skin. In some exemplary embodiments, the adhesive bond strength of the adhesive layer 14 to the substrate 12 is at least about 5% greater than the adhesive bond strength of the adhesive layer 14 to the underlying surface that the marking grid 10 is placed on. In some such embodiments, the adhesive bond strength of the adhesive layer 14 to the substrate 12 is at least about 10% greater than the adhesive bond strength of the adhesive layer 14 to the underlying surface. In yet some such embodiments, the adhesive bond strength of the adhesive layer 14 to the substrate 12 is at least about 15% greater than the adhesive bond strength of the adhesive layer 14 to the underlying surface. The current inventors have found that such differential in bond strength between the adhesive layer 14 to the substrate layer 12 relative to that of the adhesive layer 14 to the underlying surface will substantially avoid adhesive release from the substrate layer 12 that remains as residue on the underlying surface when removing the marking grid 10 from the underlying surface.

Prior to use, the adhesive layer 14 of the marking grid 10 is removably attached at an underside thereof, i.e., at an opposite side of the adhesive layer 14 relative to the substrate layer 12, to the release liner 22. One purpose of the liner 22 is to protect the adhesive layer 14, e.g., until the marking grid 10 is about to be used. In some embodiments, the liner 22 is a polymer-based liner, such as, for example, but not limited to, a polyester liner. In some embodiments, the liner defines a thickness $TH_{22}$ within the range of about 1 mil to about 10 mils, which has been found to adequately protect the adhesive layer 14. In some such embodiments, the liner defines a thickness $TH_{22}$ of about 5 mils. Other suitable materials and thicknesses can be used. While the liner 22 is intended to remain on the adhesive layer 14 until use, it also can be removed without excessive difficulty. The upper surface 24 of the liner 22 contacting the adhesive layer 14 therefore is provided with a coefficient of friction sufficiently high to mitigate slipping relative to the adhesive layer 14 prior to use, but also sufficiently low to not impede its removal from the marking grid 10 prior to use.

In some embodiments, the desired frictional properties of the liner 22 are achieved via a friction modifier on one or more of the surfaces 24, 36 of the liner. In some embodiments, the friction modifier includes a coating, such as, for example, but not limited to, a silicone coating applied to the upper and lower surfaces 24, 36 thereof. It will be appreciated by those of ordinary skill in the pertinent art that increasing the percentage of silicone applied to a surface of the liner 22 lowers the coefficient of friction of that surface and, conversely, lowering the silicone content increases the coefficient of friction. For example, increasing the percentage of silicone laid on a liner surface decreases the "grip" (increases the "slipperiness") of that surface of the liner. In such embodiments, the silicone level can be selected to achieve the desired friction. However, other suitable coating materials and means, either currently known or later developed can be used to obtain desired friction level(s), such as, for example, but not limited to, a material sold under the trademark TEFLON® by E. I. Du Pont De Nemours and Company of Wilmington, Del.

Another purpose of the liner 22 is to mitigate sticking together of stacked marking grids 10 during the manufacturing process and during storage prior to use. The opposing surface 36 of the liner 22 therefore exhibits a coefficient of friction sufficiently low to mitigate sticking to an underlying marking grid 10 when stacked during manufacture (or storage). However, a coefficient of friction of the surface 36 that is too low will cause the marking grids 10 to slip in the printing press and/or cutting machinery (explained below) during the printing and cutting stages of manufacture, which can result in misaligned printing and/or cutting. Accordingly the coefficient of friction of the surface 36 is provided so as to be sufficiently high to minimize slippage of the marking grid 10 in the printing press and/or cutting machinery to mitigate the aforementioned problems. As discussed above, this can be achieved by applying a friction modifier, e.g., a coating, to the liner surface 36, or via other suitable means and methods, as should be appreciated by those of ordinary skill in the pertinent art.

To manufacture the marking grid 10, the adhesive 14 is applied to a continuous roll of substrate layer 12 and a roll of liner 22 is releasably attached to the adhesive layer 14 using known methods as will be understood by those of ordinary skill in the pertinent art. Afterwards, the blank marking grid roll is passed through a printing press where the necessary printing, whether of radiopaque material and/or non-radiopaque material, is laid upon successive portions of the substrate layer 12, outputting successive marking grids 10 one after the other. Thereafter, the marking grid roll is cut into individual marking grids 10, such for, for example, via a die cutter.

The inventors overcame a number of obstacles to manufacture the grids 10. As discovered by the inventors, the combination of characteristics of each layer 12, 14, 22, of the marking grid 10 play an interdependent role in the successful manufacture and use of the grid. For example, the inventors discovered that the above-discussed interdependent combination of basis weight and thickness of the substrate layer 12 is beneficial to substantially accurately and sufficiently transmit a single dot of marking medium, such as, for example, ink, or substantially continuous handwriting, through the substrate layer without requiring an abnormally slow writing speed. However, when the adhesive 14 was applied to a substrate layer 12 exhibiting a thickness and basis weight as discussed above, such a thin and porous substrate layer 12 initially allowed an unacceptable amount of the adhesive to wick therethrough, rendering the upper surface 20 of the marking grid 10 too sticky for proper manufacture and use. An overly sticky marking grid 10 also caused several problems during printing of the grid lines by sticking to the printing units in the printing press, and also by sticking to adjacent marking grids 10 when stacked together after the cutting step. The inventors solved this problem by utilizing an adhesive having a thickness and viscosity that limited wicking through the substrate layer 12 to an acceptable level, such as, for example, the adhesive ARCARE 92626 sold by Adhesive Research, Inc.

In addition, in prior art methods of producing marking grids, the grid lines and respective numerals were printed onto the substrate layer prior to applying the adhesive. However, in embodiments where radiopaque material such as, for example, radiopaque ink, is printed onto the substrate layer 12 to form the grid lines 30, the inventors discovered that such a process resulted in poor printing quality because the radiopaque material would pass through the pores/gaps of the substrate layer 12 and not adequately remain on the top surface 20 of the layer 12. This not only reduced the sharpness and readability of the grid lines and numerals, but diffused the radiopaque material, diffusing and blurring the radiographic shadow on the image or scan.

Accordingly, the inventors invented a new method of applying the radiopaque material, in which the adhesive is applied to the substrate layer prior to the application of the radiopaque material. While the radiopaque material still passes through the pores/gaps in the substrate layer 12, what the inventors unexpectedly discovered is that such material lays onto the underlying adhesive layer 14, resulting in sharper and more continuous lines. What the inventors unpredictably realized is that the adhesive reduces or stops the flow of the radiopaque material, assisting to maintain the material in the desired place for readability and clearer radiographic imaging.

In some embodiments, the blank marking grids 10 are placed in a printing press (not shown) for printing onto the substrate layer 12. For example, printed material may include, without limitation, grid line numerals 32, branding graphics grid and/or part numbers. In embodiments where the grid lines 30 include radiopaque ink, the printed material may also include the grid lines 30. The liner 22 is releasably attached to the underside of the adhesive layer 14 prior to entry into the printing press to mitigate sticking of the underside 26 of the adhesive layer 14 within the press. The printing press includes flexographic and rotary screen printing stations. The rotary screen printing station includes a pre-treated printing screen mesh wrapped around a roller/drum having ink therein. A squeegee is located within the drum to press ink through the rotating screen and onto the continuously and tangentially passing roll of substrate layer 12. As will be appreciated by those of ordinary skill in the pertinent art, the printing screen undergoes an imaging process which treats all areas of the screen other than the desired printing image. Ink cannot pass through the treated areas, thereby yielding the desired printing image from the areas where ink can pass therethrough. As will also be appreciated by those of ordinary skill in the pertinent art, a printing screen mesh size compatible with the radiopaque ink is utilized in the rotary printing station, to successfully apply the proper quantity of radiopaque ink in a single pass of the marking grids 10. After printing, the marking grid 10 passes through a curing unit to dry the ink as is known. Once the marking grids have been printed and dried, the marking grids are cut into separate grids 10 for use.

In some embodiments where portions of the marking grid 10 are printed in radiopaque ink, they are printed via the rotary screen printing station of the printing press as described above. For example, where grid lines 30 are formed of radiopaque ink and printed, they are printed onto the substrate layer 12 in the rotary screen printing station and the numerals 32 may be printed there as well. In embodiments where portions of the marking grid 10 are printed in non-radiopaque ink, they are printed via a flexographic printing station of the printing press. For example, branding graphics, grid part numbers, and/or the numerals 32 (if printed in non-radiopaque ink) can be printed onto the substrate layer 12 in the flexographic printing station.

As discussed above, the marking grid 10 can be used for medical procedures. In one exemplary embodiment, the marking grid 10 is placed on a patient to assist a doctor or physician in correlating an internal point of interest identified in an image or scan with the skin surface of the patient, during a CT-guided biopsy. For purposes of example only, an exemplary point of interest POI is identified in FIG. 4. A marking may be made on the skin to precisely register, i.e., localize, a needle entry site, such as, for example, a biopsy needle, to perform a biopsy of tissue identified in the radiographic image or scan. The skin marking is to be placed so that the needle reaches the intended tissue.

Figure 5:
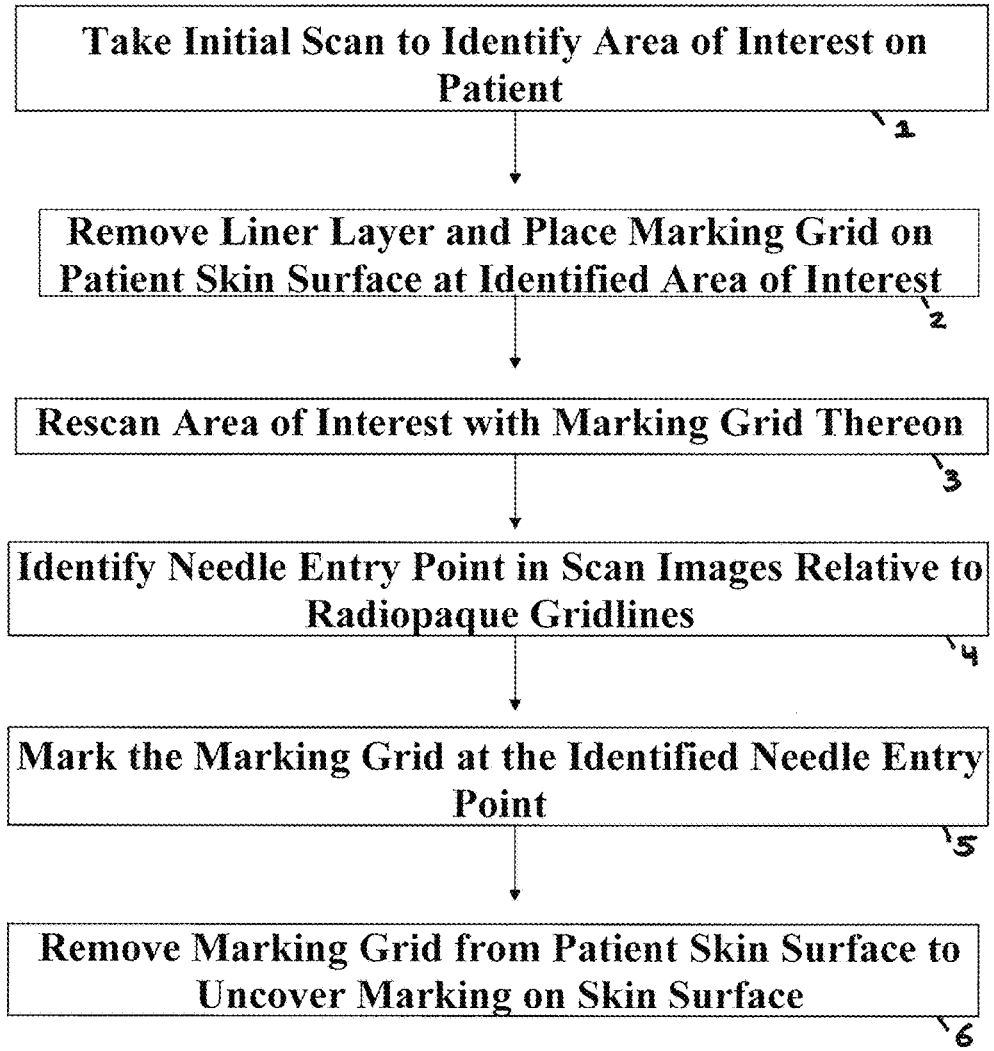
FIG. 5 is a schematic diagram of one embodiment of the steps for use of the marking grid of FIG. 2.

As shown in the embodiment of FIG. 5, a pilot scan, such as a CT scan, is first taken to identify the general area of interest in the internal tissue "IT" of the patient in step 1. Thereafter, in step 2, the release liner 22 is peeled away from the marking grid 10, thereby exposing the adhesive layer 14, and the grid 10 is placed on the skin surface of the patient over the general area of interest. The flexible nature of the marking grid 10 allows the grid to be placed substantially anywhere on the patient's body, and the grid will conform to the contour of the patient's skin substantially without wrinkling or folding. Additionally, because the adhesive layer 14 attached to the skin surface is sufficiently distributed over the underside 18 of the overlying substrate layer 12, the marking grid is securely attached to the skin surface to mitigate movement thereof or gapping between the grid and the skin or detachment from the skin during use. Those in the art will appreciate that, after the grid is attached, the contour of the patient's skin surface can change due to movement or positioning of the patient.

The marking grid 10 is placed on the patient such that the grid lines 30 are oriented in a direction substantially perpendicular to the planes of the images or scans that are to be taken. That is, the direction of the grid lines, the "x" direction, is perpendicular to the planes of the images or scans to be taken. Accordingly, the "y" direction of the grid is parallel to the plane of the image or scan. Thus, the grid lines 30 will appear in the images or scans as a series dots atop the skin surface, After the marking grid 10 is placed on the patient, the area of interest is rescanned in step 3 and the doctor or technologist will choose the most appropriate scanned cross-sectional image(s) or slice(s), such as shown, for purpose of example only, in FIG. 4. This image or slice identifies the "x" coordinate of the desired needle entry point (per the reference coordinate system of FIG. 2). As can be seen from FIG. 4, the marking grid 10 conforms to the patient's skin, and thus, the grid lines 30 are located along the patient's skin surface, without gapping therebetween. The doctor or technologist may then identify the "y" coordinate point of the desired needle entry point from the selected slice(s). The substantially continuous line width, thickness, and density of radiopaque grid lines 30, as described above, enable the lines 30 to appear in substantially all the scanned cross-sectional images of interest. Thus, in step 4, the doctor or technologist may then identify the "y" coordinate of the needle entry point in the selected image(s) relative to the grid lines 30. In step 5, having identified the location of the desired needle entry point in the scanned images relative to the grid lines/numerals, e.g., the "x" coordinate from the location at which the selected image or slice is taken (which, as described above, may be indicated by a laser directed at the patient's skin), and the "y" coordinate from the grid lines 30 appearing in the image or slice, the doctor may then utilize a marking instrument, such as, for example, but not limited to, a felt-tip ink pen to mark the substrate layer 12 of the grid 10 at a location that corresponds to the identified location/needle entry point. As discussed above, the marking may be made substantially anywhere along the upper side 20 of the substrate layer 12. The marked point will pass through the marking grid 10, substantially simultaneously and directly, and mark the underlying skin of the patient at substantially the same location and with approximately the same dimensions. Thus, the entry point can be accurately marked on the skin.

By way of example, if the doctor determines from the image or scan that the point of entry should be 3 millimeters from a particular grid line, the doctor can mark the substrate 12 with a felt tip pen at a location that is 3 millimeters from that grid line. The ink will then pass through the substrate 12 and adhesive layer 14, and mark the skin substantially at the same location and dimensions as the mark on the substrate 12.

The grid may thereafter be removed in step 6, uncovering the marking on the skin, thus identifying the biopsy needle entry point. The patient may then be prepared for the biopsy and the doctor can penetrate the skin surface at the marked point of interest to reach the internal area of interest.

As may be recognized by those of ordinary skill in the pertinent art based on the teachings herein, numerous changes and modifications may be made to the above-described and other embodiments without departing from the scope of the invention as defined in the appended claims. For example, the substrate layer may be made of other porous fabric materials, such as, for example, but not limited to, a medical grade microwoven fabric material. As another example, the liner may be made of any material capable of performing the functions of the liner as described herein. In addition, the grid may be used for other medical applications, as will be appreciated by those of ordinary skill in the art in view of the teachings herein. Further, in addition to the medical field, the marking grids may be utilized to mark any point/area of interest of any underlying surface. Accordingly, this detailed description of currently preferred embodiments is to be taken in an illustrative, as opposed to a limiting sense.

What is claimed is:

1. An image guided biopsy grid markable with a marking medium for marking the grid and a subject's skin underlying the grid with the marking medium to identify a needle entry target, the grid comprising:
    a flexible substrate defining a first side, a second side opposite the first side, and a plurality of substrate pores extending between the first and second sides that allow marking medium applied to the first side of the substrate to flow through to the second side of the substrate;
    a plurality of at least partially radiopaque grid lines spaced relative to each other on the first side of the flexible substrate, wherein the flexible substrate extends substantially throughout spaces between the grid lines, and wherein the grid lines allow marking medium applied to a grid line to flow at least one of (i) through or (ii) around the grid line and to the substrate or skin; and
    an adhesive-containing adhesive layer on the second side of the substrate having adhesive on at least portions of the second side of the substrate directly underlying the grid lines and the spaces between the grid lines, wherein the adhesive layer is configured and adapted to enable the substrate to be conformingly and removably attached to the skin substantially without gapping therebetween, and to allow marking medium flowing through the substrate to flow through the adhesive layer and onto the skin to mark the skin and identify the needle entry target.

2. A grid as defined in claim 1, wherein the grid lines define a plurality of grid line pores extending through respective grid lines that allow marking medium applied to a grid line to flow through said grid line.

3. A grid as defined in claim 1, wherein the marking on the skin is substantially the same size and shape as a corresponding marking applied to the first side of the substrate.

4. A grid as defined in claim 1, wherein the flexible substrate is substantially rectangular, and the grid lines are spaced relative to each other and extend approximately from one side of the substrate to the other.

5. A grid as defined in claim 1, wherein the grid lines are non-lead.

6. A grid as defined in claim 1, configured to allow a marking applied to the first side of the substrate or a grid line to pass substantially directly through the substrate and adhesive layer and mark the skin.

7. A grid as defined in claim 1, configured to allow a marking applied to the first side of the substrate or a grid line to pass substantially simultaneously through the substrate and adhesive layer and mark the skin.

8. A grid as defined in claim 1, wherein the adhesive covers at least about 30% of the surface area of the second side of the substrate.

9. A grid as defined in claim 8, wherein the adhesive covers substantially the entire second side of the substrate.

10. A grid as defined in claim 1, wherein the substrate is a non-woven layer.

11. A grid as defined in claim 10, wherein the non-woven substrate layer defines a basis weight within the range of about ⅖ oz/yd² to about 1 oz/yd².

12. A grid as defined in claim 11, wherein the non-woven substrate layer defines a basis weight within the range of about ½ oz/yd² to about ⅘ oz/yd².

13. A grid as defined in claim 10 wherein the non-woven substrate layer defines a thickness of less than about 25 mils.

14. A grid as defined in claim 10, wherein the non-woven substrate layer is a porous spunbond non-woven layer.

15. A grid as defined in claim 1, wherein the grid lines define a line width along a substantial portion of each line of less than about ⅛ inch.

16. A grid as defined in claim 1, wherein the grid lines define a line thickness along a substantial portion of each line within the range of about ½ mil to about 2 mils.

17. A grid as defined in claim 1, wherein the grid lines define a radiopaque material density along a substantial portion of each line of at least about 3 grams/cm³.

18. A grid as defined in claim 1, wherein the adhesive layer requires a maximum force of about 50 oz/in to peel from the skin.

19. A grid as defined in claim 1, wherein the adhesive layer defines a bond strength between the adhesive layer and the substrate that is at least about 5% greater than a bond strength between the adhesive layer and the skin.

20. A grid as defined in claim 19, wherein the bond strength between the adhesive layer and the substrate is at least about 15% greater than the bond strength between the adhesive layer and the skin.

21. A grid as defined in claim 1, wherein the adhesive defines a plurality of adhesive pores configured to allow marking medium flowing through the substrate to flow through the adhesive pores and onto the skin to mark the skin and identify the needle entry target.

22. A grid as defined in claim 21, wherein the adhesive pores define at least one of (i) substantially isolated channels and (ii) interconnected channels, configured so that the mark on the skin at least substantially corresponds in location, shape, and size to a corresponding marking applied to the first side of the substrate or a grid line.

23. A grid as defined in claim 1, wherein the adhesive layer defines a plurality of spaces between adhesive, configured to allow marking medium flowing through the substrate to flow around the adhesive and through the spaces therebetween and onto the skin to mark the skin and identify the needle entry target.

24. A grid as defined in claim 1, further comprising a release liner that is releasably attachable to an underside of the adhesive layer.

25. A grid as defined in claim 24, wherein the release liner defines a thickness within the range of about 1 mil to about 10 mils.

26. A grid as defined in claim 24, wherein the release liner is a polymer-based liner.

27. A grid as defined in claim 24, wherein the release liner includes a friction modifier on at least one of an upper side and an opposing underside thereof.

28. The grid as defined in claim 1, configured to allow a marking medium comprised of an ink or dye applied to the first side of the substrate to flow substantially directly through the substrate and adhesive layer and onto the skin to mark the skin.

29. An image guided biopsy grid markable with a marking medium for marking the grid and a subject's skin underlying the grid with a marking medium to identify a needle entry target, the grid comprising:
   a flexible substrate defining a first side and a second side opposite the first side;
   first means for allowing marking medium applied to the first side of the substrate to flow through to the second side of the substrate;
   a plurality of at least partially radiopaque grid lines located on the first side of the flexible substrate and defining spaces therebetween, wherein the flexible substrate extends substantially throughout the spaces, and wherein the grid lines allow marking medium applied to a grid line to flow at least one of (i) through or (ii) around the grid line and to the substrate or skin;
   an adhesive-containing adhesive layer on the second side of the substrate having adhesive on at least portions of the second side of the substrate directly underlying the grid lines and the spaces between the grid lines, and the adhesive layer being configured and adapted to enable the substrate to be conformingly and removably attached to the skin substantially without gapping therebetween; and
   second means for allowing marking medium flowing through the substrate to flow through the adhesive layer and onto the skin for marking the skin and identifying the needle entry target.

30. A grid as defined in claim 29, wherein the flexible substrate extends substantially throughout the spaces between the grid lines.

31. A grid as defined in claim 29, wherein the adhesive layer covers at least all portions of the second side of the substrate underlying the grid lines and the spaces between the grid lines.

32. A grid as defined in claim 29, wherein the second means is for marking the skin with a mark that is substantially the same size and shape as a corresponding marking applied to the first side of the substrate.

33. A grid as defined in claim 29, wherein the first means is a plurality of substrate pores extending between the first and second sides of the substrate, and the second means is a plurality of spaces extending through the adhesive layer between adhesive; and the grid lines are non-lead.

34. A grid as defined in claim 29, wherein the first means is a plurality of substrate pores extending between the first and second sides of the substrate, and the second means is a plurality of adhesive pores extending through the adhesive of the adhesive layer; and the grid lines are non-lead.

35. A grid as defined in claim 29, wherein the adhesive covers at least about 30% of the surface area of the second side of the substrate.

36. A grid as defined in claim 29, wherein the grid lines define third means for allowing marking medium applied to a grid line to flow through said grid line.

37. A grid as defined in claim 36, wherein the third means is a plurality of grid line pores extending through the grid lines.

38. A grid as defined in claim 29, configured to allow a marking applied to the first side of the substrate or a grid line to pass substantially directly through the substrate and adhesive layer of the grid and mark the skin.

39. A grid as defined in claim 29, configured to allow a marking applied to the first side of the substrate or a grid line to pass substantially simultaneously through the substrate and adhesive layer of the grid and mark the skin.

40. A grid as defined in claim 29, further comprising fourth means for protecting said second means.

41. A grid as defined in claim 40, wherein the fourth means comprises a release liner releasably attached to the second means.

42. The grid as defined in claim 29, configured to allow a marking medium comprised of an ink or dye applied to the first side of the substrate to flow substantially directly through the substrate and adhesive layer and onto the skin to mark the skin.

43. A method comprising the following steps:
(i) adhesively and conformably attaching a grid including a flexible substrate and an adhesive-containing adhesive layer to a person's skin, wherein the substrate includes a plurality of at least partially radiopaque grid lines spaced relative to each other on a first side of the substrate, and the adhesive layer includes adhesive on at least portions of the second side of the substrate directly underlying the grid lines and the spaces between the grid lines; and
(ii) marking the first side of the substrate with reference to one or more of the grid lines with a marking medium that passes through both the substrate and the adhesive layer and marks the skin.

44. A method as defined in claim 43, further comprising the step of imaging a portion of the person's body and substrate attached to the body, and identifying a needle entry target with reference to one or more of the grid lines, and wherein step (ii) includes marking the first side of the substrate with the marking medium at the needle entry target so that the marking medium passes through both the substrate and the adhesive layer underlying the substrate and marks the needle entry target on the skin.

45. A method as defined in claim 44, further comprising the steps of removing the substrate from the skin and inserting a biopsy needle substantially at the marked needle entry target on the skin.

46. A method as defined in claim 43, wherein the marking on the skin is substantially the same size and shape as the corresponding marking applied to the first side of the substrate.

47. A method as defined in claim 43, wherein step (ii) includes the marking medium passing through a plurality of pores extending through the substrate, and a plurality of pores or spaces between adhesive extending through the adhesive layer underlying the substrate.

48. A method as defined in claim 47, wherein step (ii) also includes the marking medium passing (i) through a plurality of pores extending through at least one grid line and/or (ii) around said at least one grid line.

49. A method as defined in claim 43, wherein step (ii) includes the marking medium passing substantially directly through the substrate and the adhesive layer to mark the skin.

50. A method as defined in claim 43, wherein step (ii) includes the marking medium passing substantially simultaneously through the substrate and the adhesive layer to mark the skin.

51. A method as defined in claim 43, wherein step (i) includes adhesively attaching the second side of the substrate to the skin with an adhesive covering substantially the entire second side of the substrate underlying the grid lines and the spaces between the grid lines.

52. A method as defined in claim 43, wherein a release liner is attached to the substrate prior to use, and further comprising the step of removing the release liner from the substrate prior to step (i).

53. A method as defined in claim 43, wherein the marking step includes applying an ink pen to the first side of the substrate.

\* \* \* \* \*